United States Patent [19]

Kawam

[11] 4,149,815

[45] Apr. 17, 1979

[54] CHEWABLE TOOTH CLEANING DEVICE

[75] Inventor: Antoine Kawam, Washington, D.C.

[73] Assignee: The Gillette Company, Boston, Mass.

[21] Appl. No.: 809,445

[22] Filed: Jun. 23, 1977

[51] Int. Cl.² ............................................. A47K 7/02
[52] U.S. Cl. .................................. 401/201; 401/132;
15/104.93
[58] Field of Search ............... 401/201, 205, 196, 131,
401/132; 15/104.93, 104.94, 244 R, 244 C

[56] References Cited

U.S. PATENT DOCUMENTS

| | | | |
|---|---|---|---|
| 3,071,476 | 1/1963 | Werft et al. ............................ | 99/135 |
| 3,124,824 | 3/1964 | Lutz ............................... | 15/104.94 X |
| 3,138,820 | 6/1964 | Sterling ............................ | 15/104.93 |
| 3,267,512 | 8/1966 | Wiley .................................... | 401/201 |
| 3,283,357 | 11/1966 | Decker et al. .................... | 15/104.93 |
| 3,297,452 | 1/1967 | Wing et al. ............................ | 99/135 |
| 3,422,184 | 1/1969 | Goldman et al. ....................... | 424/48 |
| 3,458,268 | 7/1969 | Wozab et al. ......................... | 401/261 |
| 3,590,814 | 7/1971 | Bennett et al. ..................... | 128/62 A |
| 3,902,509 | 9/1975 | Tundermann et al. ............. | 132/84 R |
| 3,903,232 | 9/1975 | Wood et al. ................... | 15/104.93 X |

*Primary Examiner*—Edward M. Coven
*Attorney, Agent, or Firm*—Richard A. Wise; R. Danny Huntington

[57] ABSTRACT

A chewable tooth cleaning device comprising from 2.45 to 9.0 cm³ of substantially closed-cell compressible polymeric foam having a substantially skin-free surface adapted to scrub exposed tooth surfaces. In particular, the polymeric foam has about 12 to 50 cells per linear centimeter, a water absorptivity of less than 1.0 mg/cm³ after being submerged in water for 24 hours, a tensile strength of at least $3.4 \times 10^5$ Pa, a compressive strength of at least $5.5 \times 10^4$ Pa at 10% deflection, and at least $8.3 \times 10^4$ Pa at 25% deflection, a tear strength of at least $1.38 \times 10^5$ Pa, and is sufficiently resilient to return to at least 90% of its uncompressed height almost immediately after being compressed to 10% of its uncompressed height.

10 Claims, 4 Drawing Figures

CHEWABLE TOOTH CLEANING DEVICE

FIELD OF THE INVENTION

This invention relates to tooth cleaning devices. The devices are useful for cleaning teeth and freshening the mouth at times when it is inconvenient to brush or use a mouthwash.

BACKGROUND OF THE INVENTION

For good oral hygiene, it is essential that deposits on the teeth be removed as often as possible. The deposition of material called "plaque" on the teeth is a two-stage process which is not entirely understood. Initially, an amorphous, non-bacterial layer is laid down composed of "pellicle", a thin film made up chiefly of an organic keratin-like substance. This is followed by a bacterial invasion and subsequent bacterial proliferation. It is generally thought that tooth decay is caused by certain types of these bacteria. Acidogenic bacteria within the plaque feed on sucrose in the diet producing acids which decalcify the teeth allowing the underlying areas to be destroyed. The plaque assists by holding these acids near the tooth surface. If not removed, the plaque will harden into calculus. If this plaque is regularly removed, the incidence of caries formation can be greatly reduced. Such deposits also contribute to halitosis, commonly known as bad breath.

A simple and effective way to remove deposits is by the use of a toothbrush or similar device. However, it is not always convenient to brush or carry mouthwash. While various dissolving tablets, breath drops, and sprays may be used for controlling bad breath, they only mask the problem, rather than removing its cause. Moreover, they do nothing to prevent decay, and in fact, some actually promote it, because the sucrose sugar incorporated as part of a tablet or lozenge may deposit as film on the teeth as the tablet dissolves. Such tablets also typically incorporate a sialagogue to stimulate the flow of saliva which helps to remove food particles from the teeth. However, this is only effective for loosely-held deposits and does little for those more stubbornly held.

Various types of chewing gums have also been suggested for use when it is inconvenient to brush. However, chewing gums do not have the rigidity needed for cleaning. This means that most of the film or plaque removal occurs on the biting surfaces of the teeth with very little, if any, on the buccal areas.

The addition of various abrasives to a gum base is suggested in U.S. Pat. Nos. 3,422,184 and 3,297,452, as a means for better cleaning the teeth. However, any gum base will fall short of effective cleaning since forces applied to the gum base result in deformation of the gum base, reducing the force actually applied to the surface of the teeth. This is true to a varying degree regardless of whether the gum base is chicle, gum acacia, as suggested in U.S. Pat. No. 3,422,184, or silicone polymer as suggested in U.S. Pat. No. 3,297,452.

The present invention overcomes the above problems by providing a chewable tooth cleaning device combining chewing properties similar to the prior art compositions with the added rigidity, shape, and surface properties necessary to effectively clean teeth.

SUMMARY OF THE INVENTION

The present invention comprises a chewable tooth cleaning device made from essentially closed-cell compressible polymeric foam. The device comprises from 2.45 to 9.0 cm$^3$ of foam having a substantially skin-free surface, 12 to 50 cells per linear centimeter, a water absorptivity of less than 1.0 mg/cm$^3$ after being submerged in water for 24 hours, a tensile strength of at least $3.4 \times 10^5$, Pa, a compressive strength of at least $5.5 \times 10^4$ Pa at 10% deflection, and at least $8.3 \times 10^4$ Pa at 25% deflection, a tear strength of at least $1.38 \times 10^5$ Pa, and is sufficiently resilient to return to at least 90% of its uncompressed height almost immediately after being compressed to 10% of its uncompressed height.

A preferred device includes an exterior surface flavor treatment and/or a flavor material tablet inserted within the interior of the device. The surface of the device preferably has ridges which are transverse or perpendicular to the longest dimension of the device.

BRIEF DESCRIPTION OF THE DRAWINGS

In the accompanying drawing, a preferred embodiment of the invention is illustrated. Obviously, changes in form may be made within the scope of the invention.

DETAILED DESCRIPTION OF THE INVENTION

Figure 1:
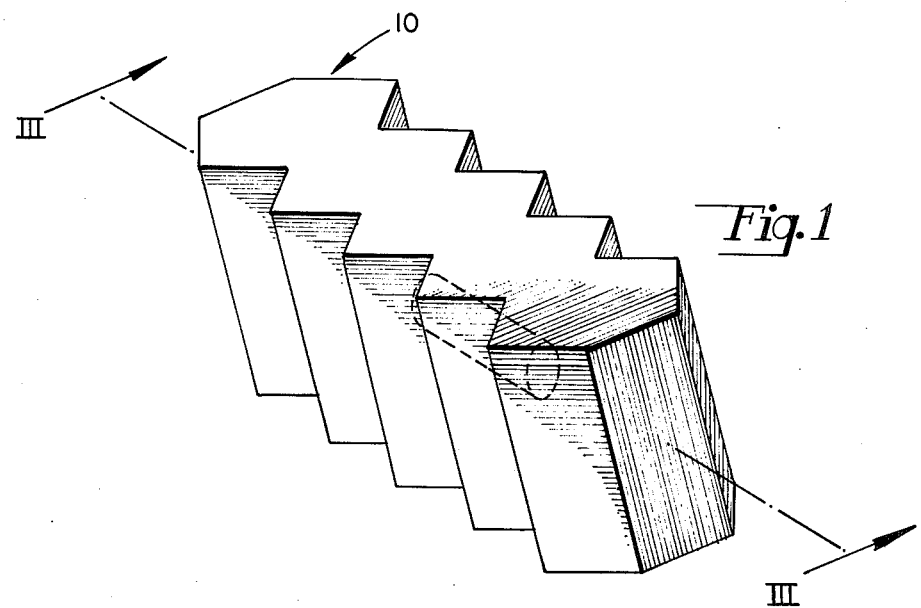
FIG. 1 is a perspective view of a tooth cleaning device embodying this invention.
Figure 2:
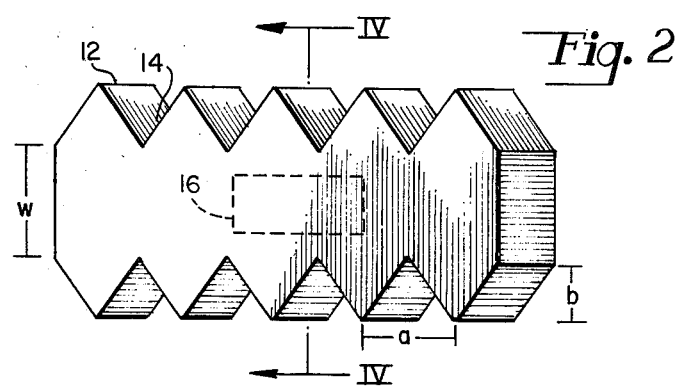
FIG. 2 is a view of the device of FIG. 1 from a different perspective.
Figure 3:
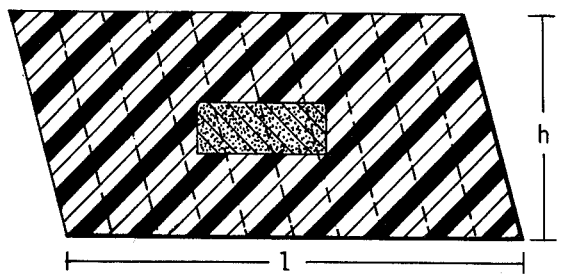
FIG. 3 is a cross-sectional view along axis III—III shown in FIG. 1.
Figure 4:
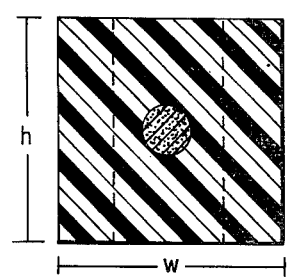
FIG. 4 is a cross-sectional view along axis IV—IV shown in FIG. 2.

There are a number of specific properties necessary to make a material useful for tooth cleaning while at the same time providing a pleasant and refreshing sensation in the mouth during chewing. These characteristic properties have been found in certain foamed polyethylenes. However, it should be pointed out that foams of different chemical structure possessing the requisite physical properties are also useful in the practice of the present invention since the device cleans the teeth by physical action rather than by any chemical reaction with the teeth.

The first criterion is that the foam must be non-toxic and otherwise physiologically safe in use. Another property is the degree to which the foam can absorb water. If too much water, in the form of saliva, can be absorbed by the foam, an unpleasant sensation, which can be described as "chewing a wet rag", will be noticed. Thus, it is important that there should be absorbed less than 1 milligram of water per cubic centimeter of foam after 24 hours of immersion.

The important properties with respect to the foam's physical structure are porosity and cell size. The foam must be essentially closed-cell and have cell sizes which fall within a specific narrow range. If the cells are too fine, the foam tends to feel smooth and slippery when chewed and doesn't provide good cleaning. If the cells are too coarse, the foam will feel scratchy and irritate the gums. I have found that foams having an average cell size between 12 and 50 cells per linear centimeter are useful in the practice of my invention. The preferred range is 20 to 30 cells per linear centimeter.

To be useful in this invention, foams must fall within a very specific range of material compression strength to insure proper cleaning comfort and a desirably rapid rate of shape recovery. The chewable foam base must compress to only a certain extent when a moderate chewing force is applied. If excessive force is needed to compress the device, the jaws will become fatigued. If too little force is required for compression, the device will "bottom out". A device "bottoms out" if it reaches its point of maximum compression before the person's jaws have exerted their peak force. While being chewed, the foam may be subjected to 500 or more compressions with varying forces and must resist tearing as well as fatigue. It must be stiff enough to resist bottoming, yet it must be capable of some 90% deflection while being compressed during the chewing process and still recover immediately to at least 90% of its original height. By "deflection", I mean the amount by which the foam has been compressed compared to its original dimension. Thus, a piece of foam, originally 10 cm thick, which has been compressed to 2.5 cm thick would be said to have undergone a 75% deflection. To conform to the above requirements, it is necessary that the compressive strength of the foam, as measured by ASTM-Standard D-1056, be such that a minimum applied force of $5.5 \times 10^4$ Pa is required to obtain a 10% deflection of the foam, a minimum applied force of $8.3 \times 10^4$ Pa is required for a 25% deflection, and a minimum applied force of $1.38 \times 10^5$ Pa is required for a 50% deflection. The preferred materials undergo a 25% deflection when a force between $1.03 \times 10^5$ Pa is applied.

The tensile strength, measured in the manner described in ASTM Standard D-1056, must be in the range from $3.4 \times 10^5$ to $8.3 \times 10^5$ Pa at 100 to 200% elongation.

Another important property is the "tear strength" which is the force necessary to initiate or to continue tearing of the foam. Due to the grinding action of the teeth, it is necessary that the foam have a tear strength, measured in the manner described in Millitary Standard 670-B—Sec. 5.1.3.2. of a minimum of $1.38 \times 10^5$ Pa.

The character of the surfaces of the foam which contact the teeth is also important. They should be essentially free from polymeric skin and preferably be blade cut to a configuration such that a certain minimum number of open cells are exposed on the surface for improved frictional efficiency and thereby better cleaning. The open cells produced on the surfaces by such a procedure are also necessary if one desires to coat the surface with a flavor material as described below.

While a foam having the properties described above will clean teeth effectively when chewed, the cleaning can be enhanced by proper selection of size and shape in forming the device. The size should be such that the risk of blocking the windpipe if accidentally swallowed is minimized. The minimum dimension of the device should be in the range from about 0.3 cm to 1.9 cm, more preferably about 1.0 cm to 1.6 cm. The device may take any shape including, but not limited to, a rectangular solid, a cube, a sphere, or a cylinder, although the use of other less regular shapes is within the scope of the invention. Regardless of the shape used, the volume should fall in the range from 2.45 cm$^3$ to 9.0 cm$^3$. For enhanced cleaning, it is necessary to have a device that will clean the chewing surfaces of the teeth while at the same time cleaning labial and lingual surfaces. By labial surface, I mean the tooth surface in contact with the lips, while the lingual surface refers to the tooth surface in contact with the tongue. One means of cleaning the surfaces between the teeth is to employ projections such as ridges or peaks on the device. It is of additional advantage if the projections are spaced in such a way that the linear distance from the tip of one projection to the tip of an adjacent projection is approximately the same as the average linear distance between the space on each side of an adult tooth. That distance is about 0.5 cm in the average adult.

FIGS. 1–4 show a device 10 having a series of ridges 12 and valleys 14. Before serrating, the device 10 is a parallelepiped of the dimensions 1.25 cm wide (w), by 1.25 cm high (h), by 2.5 cm long (l).

At least one face of the device 10 preferably has projections which may take any form desired, the ridges 12 in FIGS. 1–4 being the preferred embodiment. The ridges 12 are preferably arranged transverse to the longest dimension of the device, which is l in the preferred embodiment. The distance, a, between the ridges, 12, may range from about 0.4 cm to 0.6 cm, and the depth, b, of the valleys 14 from about 0.3 cm to 0.5 cm. Parameters a and b should be chosen to produce a device which cleans the curved lingual and labial surfaces of a tooth. The distance around the curved buccal surface of the average adult tooth in about 0.95 cm. Thus, a and b should be chosen such that the distance from the tip of a ridge to the tip of the next adjacent ridge, measured by following the contour of the foam surface, is about 0.95 cm. Such a design allows cleaning of the labial and lingual tooth surfaces via rubbing against the inter-ridge surfaces of the device, while the interproximal surfaces are simultaneously cleaned by the rubbing action of the ridges.

Shown within the interior of the device 10 is a flavor insert 16. The insert 16 and its method on insertion are described below.

While a chewable foam device such as described above does an effective job of cleaning the teeth, it is desirable to incorporate flavoring agents or other ingredients such as surfactants to improve surface wetting, bacteriocides, anti-caries agents, or breath-freshening deodorizers. Flavoring agents also act as a sialagogue, additionally helping to clean the teeth as described above. Flavoring agents or other ingredients can be incorporated by means of a surface coating, by placing the ingredients inside the device, or a combination of both.

In choosing a system, it is desirable that the flavoring agent be released at a relatively constant rate during the period of time, approximately three minutes, that the device would typically be chewed. In addition to the rate of release, the intensity of the flavor must be controlled. If the flavor is too strong, it will be objectionably sharp and biting. If the flavor is too weak, the taste buds will become desensitized during the period of use with a concomitant loss in flavor sensation. The amount of flavor must thus be adjusted to a point between the two extremes. The preferred amount is a question of individual taste and varies according to the type of flavoring agent used, e.g., spearmint, peppermint, cinnamon, etc. The most effective way to set flavor limits is by field testing.

The flavoring agent used as an exterior surface coating consists of two principal components, a spice and a binder. Useful examples of spices are mint oils, such as peppermint, spearmint, and the like, essential oils extracted from oranges, lemons, and other fruits, and bean-derived flavors such as coffee, cocoa, and the like. Typical binders which can be used to encapsulate the spice by processes well known to those skilled in the art, thus forming a powder, are gum arabic and dextrin. Typical spice to binder ratios are 1:5 to 1:50, with the amount of flavor material retained on the surface of the device being directly proportional to the amount of binder present. The deposition of a flavor material may also be improved by the incorporation of well known anti-caking agents such as silica. Finally, it is possible, if one desires, to add a sweetener such as saccharin.

When an exterior surface coating is applied by tumbling, the tumbling temperature, speed, duration, and concentration of the flavor material or other ingredient in the tumbling vessel influence the amount of flavor deposited. With respect to tumbling speed, I have found that increasing speeds up to 33 rpm increase the add-on of powder but that no substantial increase occurs when faster speeds are used. Using 33 rpm, it was found that increasing the weight ratio of flavor material to foam from 1:2 to 5:2 increased the amount of add-on by approximately 50% with very little increase when more flavor material is used.

With respect to the time of tumbling, increasing from one minute to five minutes adds-on an additional 50% of flavor material. However, extending the time beyond five minutes results in only an additional 10% add-on. Finally, increasing the temperature of the tumbling vessel from room temperature to 86° C. results in about a 20% increase in add-on. By adjusting the various factors, it is possible to add on any desired amount of flavor material.

Chewing a device having a surface treatment such as that described previously, releases flavor over a period of approximately one minute. Since some people may desire to chew the device for a longer period of time, it is of additional advantage to extend the flavor by inserting flavor material within the interior of the device. Since the properties which make the chew functional stem from its closed-cell structure, it is important that any method used for inserting flavor within the interior not substantially affect the closed-cell nature of the foam. A preferred method for inserting flavor material involves making a slit along one of the non-ridged surfaces of the device and inserting a tablet. The tablet is composed of flavor material similar to those described above except that the anti-caking agent is omitted, and to facilitate tableting, sorbitol or xylitol powder is substituted for some of the dextrin powder. Xylitol is additionally useful in that it has been suggested that it may aid in remineralization of tooth enamel thereby healing tooth decay. After insertion of the tablet, a heated iron tool or other heating means is run along the upper edge of each slit surface and the surfaces lightly pressed together to seal them.

Upon chewing a device with an inserted tablet, the cell structure will gradually be broken down by the teeth, thereby slowly releasing the flavor. Insertion of flavor material in the above manner extends the flavor from one and one half to two minutes. By using both a surface coating and an inserted tablet, it is possible to obtain a device which delivers flavor over an approximately three-minute period.

EXAMPLE I

A tooth cleaning device, as shown in FIG. 1, 2.5 cm long, 1.25 cm wide, and 1.25 cm thick, was blade cut from a radiation cross-linked, closed-cell polyethylene foam, sold under the trade name "Plastazote (PO-16)", manufactured by Expanded Rubber & Plastics, Ltd. Bakelite Xylonite Co., London, England, having the following properties:

Cell Size: 20–30 cells/linear cm
Water Absorption: less than 1.00 mg/cm$^3$ (24 hrs)
Compression/Deflection: about $1.17 \times 10^5$ Pa at 25% deflection
Tensile Strength: $5.52 \times 10^5$ Pa
Tear Strength: $1.3 \times 10^5$ Pa The resultant cleaning device was then evaluated as follows:

A group of 22 subjects was asked to brush their teeth with toothpaste and a brush. Each subject rinsed his mouth with a plaque disclosing dye and then brushed again to ensure removal of all plaque. Plaque was then allowed to accumulate over a 72-hour period. At the end of that time, the subjects again used a plaque disclosing dye and the level of plaque on their teeth was rated by a clinical investigator using the Clinical Plaque Index described in detail in "Alteration of Plaque in Caries Prevention" by Ralph R. Lobene, published in the Journal of Oral Medicine, Vol. 27, Issue 1, pp. 2–6, 1972.

Half of the subjects were then asked to chew one of the devices of Example I and discard it after chewing for about three minutes, after which the level of remaining plaque was again rated as above. The results of this clinical trial demonstrated that a statistically significant amount of dental soft plaque could be removed from the buccal surfaces of natural teeth by the use of the device in Example I.

EXAMPLE 2

A device as described in Example 1, was coated with about 30 mg of flavor material consisting of 3% spearmint oil encapsulated in 97% dextrin powder. The coating was performed by tumbling the device for ten minutes at 24° C. and 33 rpm with a 7:1 weight ratio of flavor material to foam.

The resulting device, when chewed, effectively cleaned the teeth, leaving a pleasant and refreshing taste in the mouth.

EXAMPLE 3

A device as described in Example 1 was modified by inserting within it a 40 mg tablet containining 4% spearmint oil, 16% dextrin, 3% saccharin, and 77% sorbitol powder. A slit 1.25 cm long and about 1.0 cm deep was made along the flat side of axis III—III as shown in FIG. 1. The tablet was inserted and a wedged-shaped iron tip was passed over each slit surface at a 0.1 to 0.15 cm depth. The two heated surfaces were immediately, but lightly, pressed together to form a seal. The resulting device, when chewed, cleaned the teeth, leaving the mouth cleaned and refreshed.

EXAMPLE 4

A tooth cleaning device as shown in FIG. 1, 2.5 cm long, 1.25 cm wide, and 1.25 cm thick was blade cut from a peroxide cross-linked, closed-cell polyethylene foam, sold under the trade name Minicel L-400 (Haveg Industries, a subsidiary of Hercules, Inc., Wilmington, Del.) having properties falling within the above described ranges.

A tablet of flavor material was then inserted within the device as described in Example 3 and the surface was coated as described in Example 2. The resulting device, when chewed, effectively cleans the teeth, releasing its flavor over a three-minute period, leaving the mouth feeling clean and refreshed.

Other embodiments will occur to those skilled in the art and are within the following claims.

What is claimed is:

1. A shape retaining chewable tooth cleaning device comprising from 2.45 to 9.0 cm$^3$ of a substantially closed-cell compressible polymeric foam, having a substantially skin-free surface, said polymeric foam having a cell size of about 12 to 50 cells per linear centimeter a water absorptivity of less than 1.0 mg/cm$^3$ after being immersed for 24 hours, a tensile strength of at least $3.4 \times 10^5$ Pa, a compressive strength of at least $5.5 \times 10^4$ Pa at 10% deflection and at least $8.3 \times 10^4$ Pa at 25% deflection, a tear strength of at least $1.38 \times 10^5$ Pa, and being sufficiently resilient to return to at least about 90% of its umcompressed height substantially immediately after being compressed to about 10% of said uncompressed height.

2. The device of claim 1 wherein said foam has a cell size of about 20 to 30 cells per linear centimeter.

3. The device of claim 1 wherein said foam has a compressive strength of about $1.03 \times 10^5$ to $1.38 \times 10^5$ Pa at 25% deflection.

4. The device of claim 1 wherein said foam is polyethylene foam.

5. The device of claim 1 wherein said surface contains a plurality of projections from about 0.4 cm to 0.6 cm apart.

6. The device of claim 5 wherein said projections are ridges arranged transverse to the longest dimension of said device, said ridges being from about 0.4 cm to about 0.6 cm apart and separated by valleys from about 0.3 cm to about 0.5 cm deep.

7. A chewable tooth cleaning device as described in claim 1 comprising, in addition, an exterior surface flavor coating.

8. A chewable tooth cleaning device as described in claim 7, said flavor coating comprising, in addition, a sweetening agent selected from the group consisting of sorbitol and xylitol.

9. A chewable tooth cleaning device as described in claim 1 comprising, in addition, a tablet composed of flavor material sealed within the interior of said device.

10. A method for cleaning teeth, comprising the chewing of a shape retaining chewable tooth cleaning device comprising from 2.45 to 9.0 cm$^3$ of a substantially closed-cell compressible polymeric foam, having a substantially skin-free surface, said polymeric foam having a cell size of about 12 to 50 cells per linear centimeter, a water absorptivity of less than 1.0 mg/cm$^3$ after being immersed for 24 hours, a tensile strength of at least $3.4 \times 10^5$ Pa, a compressive strength of at least $5.5 \times 10^4$ Pa at 10% deflection and at least $8.3 \times 10^4$ Pa at 25% deflection, a tear strength of at least $1.38 \times 10^5$ Pa, and being sufficiently resilient to return to at least about 90% of its uncompressed height substantially immediately after being compressed to about 10% of said uncompressed height.

* * * * *